United States Patent [19]

Eberle

[11] Patent Number: 4,591,486
[45] Date of Patent: May 27, 1986

[54] DEVICE SEDIMENTATION OF A SAMPLE LIQUID AND A SAMPLE EXAMINATION SYSTEM

[76] Inventor: Günter Eberle, Gartenstrasse 100, 7200 Tuttlingen, Fed. Rep. of Germany

[21] Appl. No.: 607,169

[22] Filed: May 4, 1984

[30] Foreign Application Priority Data

May 4, 1983 [DE] Fed. Rep. of Germany ....... 3316335

[51] Int. Cl.⁴ ............................ G01N 9/30; B01L 3/00
[52] U.S. Cl. ...................................... 422/72; 422/102
[58] Field of Search .................. 422/72, 102; 356/246; 494/16, 17

[56] References Cited

U.S. PATENT DOCUMENTS 4,066,414 1/1978 Selby ................................... 422/102
4,427,634 1/1984 Truglio ........................... 422/102 X Primary Examiner—Michael R. Lusignan
Attorney, Agent, or Firm—Antonelli, Terry & Wands

[57] ABSTRACT

The method for sedimentation of part of a sample liquid on a slide by centrifuging a sample tube containing the sample liquid consists in the fact that the separation of the sample liquid into a sedimentation product and a supernatant and the coating of the slide with the sedimentation product is accomplished in a single work step during centrifugation. A plurality of successive work steps of a conventional nature is thereby avoided, because the sample tube containing the sample liquid is designed in the form of a centrifuge tube sealed by a releasable closure, against whose inner end, pointing into the centrifuge tube, the slide is releasably fastened.

18 Claims, 5 Drawing Figures

DEVICE SEDIMENTATION OF A SAMPLE LIQUID AND A SAMPLE EXAMINATION SYSTEM

The invention relates to a method and device for a sedimentation of parts of a sample liquid on a slide by centrifuging a sample tube containing the sample liquid, and separation of the sample liquid into a sedimentation produced and a supernatant, as well as a system for examining the sample.

In previously centrifuging processes, there is the problem that it is desired to sediment a certain sedimentation product of a sample liquid on a slide, in order to evaluate this slide optically. Such evaluation is known in urology, hematology, cytodiagnostics, and histology.

In the past, the procedure was as follows: the sample liquid was initially prepared in a separate sample tube. This was accomplished, for example, by suspending the sample taken from the body in a sample liquid. The sample liquid was then placed in a centrifuge tube and subjected to a centrifuging process, so that the sediment and a supernatant formed after completion of the centrifuging process. The supernatant was discarded and the sediment transferred to a slide. The transfer to the slide was accomplished, for example, by placing a drop of the sediment on the slide, spreading it thereon, and making it adhere thereto by a fixative treatment. The slide was then subjected to additional, e.g. optical, examination.

This conventional procedure is very laborious, time-consuming, and expensive since it is necessary first of all to perform a centrifuging process, then separate the supernatant and sediment by hand, and then transfer the sediment to the slide.

The goal of the present invention is to considerably simplify the method steps described above. To achieve the stated goal, the invention is characterized by the fact that separation of the sample fluid into a sedimentation product and a supernatant, and coating the slide with a sedimentation product, take place in a single work step during centrifugation.

Therefore, the present invention breaks completely new ground since the previously described conventional successive and manually executed work steps are now automatically handled according to the invention during the centrifuging process in a single work step.

In accordance with the present invention, sample tube containing the sample liquid is formed as a centrifuge tube, provided with a releasable lock, to whose inner end, pointing into the centrifuge tube, the slide is removably fastened.

According to the invention, a centrifuge tube made in this form with a lock and slide integrated therein is placed with its lock side downward in a trunnion carrier on a centrifuge rotor. The centrifuge is then turned on and the carrier swings outward in the usual fashion, whereby the sample liquid is forced against the slide and the sediment is automatically deposited on the slide as the centrifuging process proceeds.

During the centrifuging process, therefore, the sediment is automatically deposited on the slide without the previously described transfer step being required.

After the centrifuging process is complete, the centrifuge tube is inverted so that all of the liquid flows downward. The sealing cap containing the slide is removed and the slide removed from the sealing cap. The slide is now ready for immediate further investigation because it is already coated with sediment.

An additional important advantage of the method and apparatus of the present invention resides in the fact that the slide need only be as large as is required for placing in the centrifuge tube. This is quite critical for storage and documentation by comparison with previously known slides. Previously known slides consist of elongated rectangular pieces of glass of which only a small percentage is the actual field (observation field). This investigation area under the best conditions makes up 20–30% of the total area of the slide.

A slide which is made small according to the invention is very important for storage and documentation because all superfluous areas, like those in previously known slides, can be eliminated. The marking area associated with the slide is applied in another fashion to be described hereinbelow.

According to the invention, therefore, a relatively small slide is proposed which contains the sample information as such and the remaining area of the glass is eliminated.

This not only results in a saving of space but also in a considerable cost saving.

Another important advantage is that the centrifuge tube with the screw cap and the slide located therein can be a single article for shipment. Considerable time and expense is saved in this manner as well.

It is also important that at the location where the sample is collected, namely from all body openings and all parts of the human body, the collected sample can be placed in the centrifuge and the centrifuge tube can then be sent away, always remaining closed until the sediment is deposited on the slide during the centrifugation process and the slide is removed from the centrifuge tube. This results in a considerable improvement in sample safety and protection against mixup/confusion between samples.

Another embodiment of the invention consists of a sample smear being placed directly in the centrifuge tube with the aid of a sample carrier, such as for example a cotton swab whereby the sample carrier is dipped in the sample liquid and the sample carrier (e.g. the cotton swab) is firmly fastened in the sample tube and shipped together with the latter. The centrifuge tube is then not opened in the laboratory but the screw cap is centrifuged as well, whereby it remains in its holder. Once again, there is no need to open the centrifuge tube until the slide is fully coated.

Another important feature of the invention is that the slides removed from the sample tube and completely coated are placed on cards or strips of material at intervals, whereby an appropriate marking is added to each slide on the card. The slides are mounted on the cards or strips of material by adhesive or by placing them in prepared openings. In this way, strips of slides of any length can be prepared, which can then be processed further like a belt in automatic diagnostic machinery.

Therefore, the invention not only provides a novel centrifuging system which saves both time and expense, but also a sample examination method characterized by the fact that a plurality of slides is fastened at intervals to a card, whereby a marking area on the card is associated with each slide.

The subject of the present invention not only follows from the subject of the individual claims but also from the combination of the individual claims with each other. All of the information and features disclosed in the documents, especially the three-dimensional structures shown in the drawings, are claimed as the invention, to the extent that they are novel with respect to the state of the art either individually or in combination.

In the following, the invention is described in greater detail with reference to drawings that show a plurality of embodiments. Further features and advantages of the invention that are essential thereto will be apparent from the drawings and their description.

Figure 1:
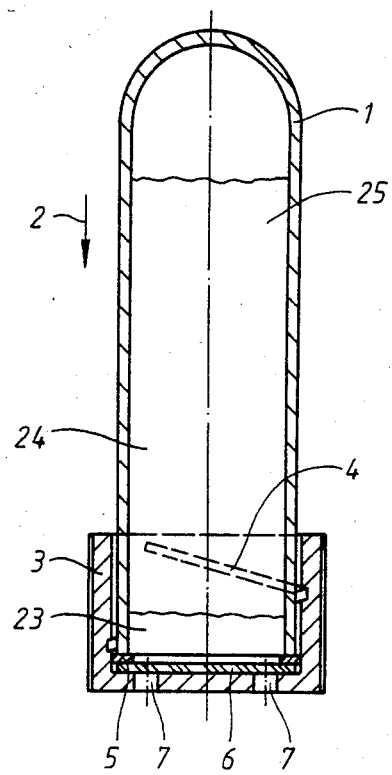
FIG. 1 is a longitudinal cross-sectional view of a first embodiment of a centrifuge tube.

Referring now to the drawings wherein like reference numerals are used throughout the various views to designate like parts and, more particularly, to FIG. 1, according to this figure, a centrifuge tube 1 is provided with a screw thread 4, on which a cap 3, with a matching internal thread, is threadably attached. Slide 6, made of glass, is disposed on the inside of screw cap 3, with the slide being sealed by a sealing disk 5 against the edge of centrifuge tube 1 and the seal of screw cap 3.

Figure 4:
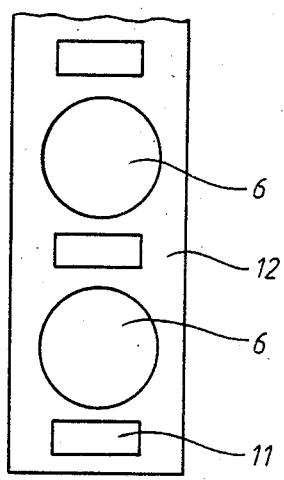
FIG. 4 is a top view of a card with slides and marking areas thereon.

Centrifuge tube 1, filled with sample liquid 25, is now inserted into a trunnion carrier of a centrifuge with screw cap 3 facing downwardly, whereby the trunnion swings out during the centrifugation process in known fashion and centrifuge tube 1 assumes a horizontal position. The centrifugal force then acts in the direction of arrow 2 on sample liquid 25 which separates, after completion of the centrifuging process, into a sedimentation product 23 and a supernatant 24. The sedimentation product is firmly deposited on slide 6 as a result of the centrifugal force acting in the direction of arrow 2. After the centrifuging process is complete, the centrifuge tube 1 is removed from the centrifuge and inverted, whereby those parts of the sedimentation product 23 which have not been deposited on the slide mix once more with supernatant 24 and flow back into the rounded bottom of centrifuge tube 1. Screw cap 3 is then removed and a tool inserted through ejection openings 7 in the cover of screw cap 3. The tool may, for example, being in the form of a fork with tines, and the slide 6 is thus removed from the interior of screw cap 3. The coated slide 6 is then placed on the card 12 shown in FIG. 4 and simultaneously aligned with a marking area 11. Card 12 can be of any length so that a plurality of slides can be fastened sequentially and at spaced intervals on card 12. The card 12 is advantageously made in the form of a machine-processable belt of a predetermined length.

Figure 2:
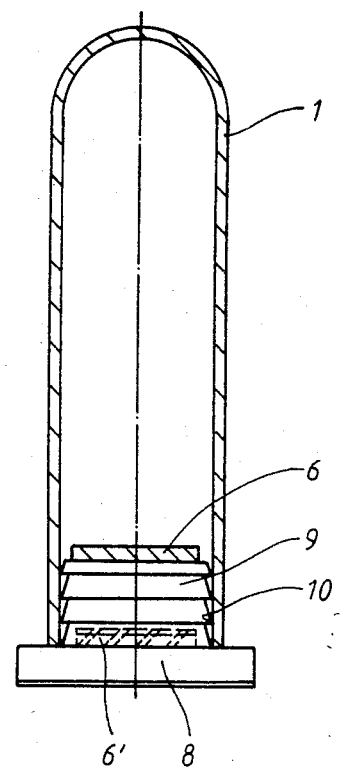
FIG. 2 is a longitudinal cross-sectional view a second embodiment of a centrifuge tube of the present invention.

As shown in FIG. 2 the centrifuge tube 1 may be closed by a stopper 8, with the stopper 8 being provided with barbs 10 on its inner part 9, which barbs press in a sealing fashion, against an inner surface of centrifuge tube 1. The slide 6 can be mounted on the end of inner part 9 of stopper 8 or, as shown in Phantom line a slide 6' disposed on the bottom of stopper 8. As soon as slide 6 is placed on the end of inner part 9, it must be supported against the action of the centrifugal force by ribs, not shown in greater detail, or other reinforcements against the bottom of the stopper.

Figure 3:
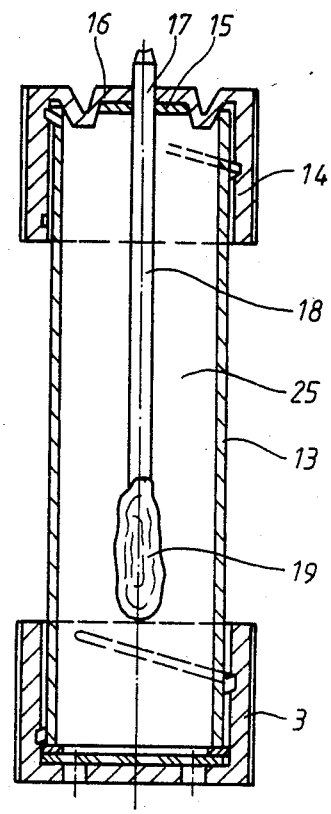
FIG. 3 is a longitudinal cross-sectional view of a third embodiment of a centrifuge tube of the present invention with the sample carrier inserted.

As shown in FIG. 3, a bottom screw cap of the type shown on one end of FIG. 1 is provided in a centrifuge tube 13, with the other end of centrifuge tube 13 is closable by an additional screw cap 14. A sealing disk 15 is disposed against an inner surface of the cap 14, with a bore 17 for insertion of rod 18 of a cotton swab 19 being provided in a cover portion 16 of the cap 14. In this manner, a cotton swab 19, coated with the sample under test, is introduced by its rod 18 into the bore 17 of the through sealing disk 15 and retained therein. The fastening is accomplished in any fashion by, for example pinching, welding, gluing, or by thermal deformation of the material of the rod 18.

When screw cap 3 is opened, a test medium such as alcohol is added to centrifuge tube 13 and screw cap 3 is re-closed. Centrifuge tube 13 prepared in this manner is then ready for shipment and can be centrifuged immediately, with cotton swab 19 remaining in centrifuge tube 13.

Figure 5:
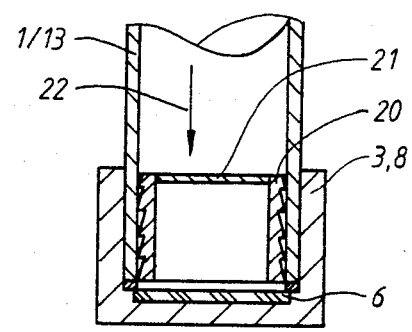
FIG. 5 is a partial longitudinal cross-sectional view of a fourth embodiment of a centrifuge tube of the present invention.

FIG. 5 shows special type of stopper that can be used with the embodiments shown in FIGS. 1-3. A hollow cylindrical plug 20 abuts the interior of screw cap 3, 8, with an opening in the stopper being closed by a an inner screen 21. The arrangement of an inner screen 21 has the important advantage that foreign bodies of a certain size can be kept away from the slide 6 during the centrifuging process. The flow of liquid is then directed in the direction of arrow 22 through the inner screen 21 during the centrifuging process and therefore reaches slide 6 in filtered form, upon which sedimentation product 23 is deposited.

I claim:

1. Device for sedimentation of a sample liquid, the device comprising a sample tube for containing the sample liquid, said sample tube being formed as a centrifuge tube, a releasable closure means mounted on one end of the centrifuge tube, and a slide means releasably fastened to an inner surface of the closure means for receiving the sedimentation of the sample liquid, said slide means extending transversely of a longitudinal axis of the centrifuge tube with a first surface of said slide means being in abutment with an inner surface of the closure means.

2. Device according to claim 1, wherein said releasable closure means includes a threaded cap.

3. Device according to claim 1, wherein said releasable closure means includes a stopper member.

4. Device according to claim 2, further comprising a sealing disk disposed between a circumferential end edge of the centrifuge tube and a second surface of said slide means.

5. Device according to claim 2, further comprising an inner hollow cylindrical plug extending into the centrifuge tube, said cylindrical plug being connected to said threaded cap, and wherein a screen means is mounted on an open end of said cylindrical plug for filtering the sedimentation in the sample liquid.

6. Device according to claim 5, wherein said slide means is fastened on the hollow cylindrical plug.

7. Device according to claim 6, wherein the centrifuge tube is open at both ends thereof, with said releasable closure means closing one end of the tube, and an additional closure means is provided for closing the second end of the tube, said additional closure means being connected with a sample carrier means immersed in the sample liquid.

8. Sample examination system for examining slides coated with a sedimentation product of a sample liquid contained in a sample tube subjected to a centrifuging process for separating the sample liquid into the sedimentation product and a supernatant so as to coat the slide with the sedimentation product in a single work step during the centrifuging process, the system comprising a card provided with a plurality of marking areas, each of the marking areas being provided with individual markings associated with each slide, said marking areas being arranged at a predetermined spacing from each other, with said coated slides being respectively mounted in the marking areas provided on said card.

9. Sample examination system according to claim 8, wherein the card is a machine-processable belt of a predetermined length.

10. Device according to claim 1, wherein the centrifuge tube is open at both ends thereof with the releasable closure means closing one end of the tube, and an additional closure means is provided for closing the second end of the tube, said additional closure means being connected with a sample carrier means immersed in the sample liquid.

11. Device according to claim 3, further comprising a sealing disk disposed between a circumferential end edge of the centrifuge tube and a second surface of said slide means.

12. Device according to claim 2, further comprising an inner hollow cylindrical plug extending into the centrifuge tube, said cylindrical plug being connected to said threaded cap, and a screen means mounted on an open end of said cylindrical plug for filtering the sedimentation in the sample liquid.

13. Device according to claim 12, wherein the slide means is fastened on the hollow cylindrical plug.

14. Device according to claim 1, wherein the centrifuge tube is open at both ends thereof with the releasable closure means closing one end thereof, an additional closure means is provided for closing the second end of the tube, said additional closure means being connected with a sample carrier means immersed in the sample liquid.

15. Device according to claim 3, further comprising an inner hollow cylindrical plug extending into the centrifuge tube, said cylindrical plug being connected to said stopper member.

16. Device according to claim 15, wherein said slide means is fastened on the hollow cylindrical pump.

17. Device according to claim 15, wherein said slide means is disposed in said hollow cylindrical plug.

18. Device according to claim 5, wherein said slide means is disposed in said hollow cylindrical plug.

* * * * *